(12) United States Patent
Tan

(10) Patent No.: US 7,435,237 B2
(45) Date of Patent: Oct. 14, 2008

(54) MIXING SYRINGES WITH BREAKABLE SEPTUMS

(75) Inventor: Sharon Mi Lyn Tan, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 646 days.

(21) Appl. No.: 10/453,144

(22) Filed: Jun. 2, 2003

(65) Prior Publication Data

US 2004/0243055 A1 Dec. 2, 2004

(51) Int. Cl.
*A61M 5/00* (2006.01)
(52) U.S. Cl. ...................................... 604/187
(58) Field of Classification Search ............... 604/86, 604/88, 89, 416, 187, 83, 82, 87, 90, 91
See application file for complete search history.

(56) References Cited

U.S. PATENT DOCUMENTS

| 4,040,420 | A | | 8/1977 | Speer | |
|---|---|---|---|---|---|
| 4,055,177 | A | * | 10/1977 | Cohen | 604/88 |
| 4,381,380 | A | | 4/1983 | LeVeen et al. | |
| 4,738,660 | A | | 4/1988 | Lucas | |
| 5,102,388 | A | * | 4/1992 | Richmond | 604/88 |
| 5,476,449 | A | * | 12/1995 | Richmond | 604/87 |
| 5,637,087 | A | * | 6/1997 | O'Neil et al. | 604/82 |
| 5,989,215 | A | * | 11/1999 | Delmotte et al. | 604/82 |
| 6,386,872 | B1 | * | 5/2002 | Mukasa et al. | 433/90 |
| 6,423,050 | B1 | * | 7/2002 | Twardowski | 604/500 |

FOREIGN PATENT DOCUMENTS

| EP | 0 272 656 | 6/1988 |
|---|---|---|
| EP | 0 711 570 | 5/1996 |
| NL | 273 113 | 3/1964 |

OTHER PUBLICATIONS

International Search Report for PCT/US2004/016693, mailed Oct. 5, 2004.

* cited by examiner

*Primary Examiner*—Nicholas D. Lucchesi
*Assistant Examiner*—Christopher D Koharski
(74) *Attorney, Agent, or Firm*—Fish & Richardson P.C.

(57) ABSTRACT

Methods and systems for treating medical devices. The treatment includes introducing liquid antimicrobial agents into medical devices.

13 Claims, 6 Drawing Sheets

MIXING SYRINGES WITH BREAKABLE SEPTUMS

TECHNICAL FIELD

The invention relates to medical devices, such as, for example, those that can be communicable with a body, and methods of treating medical devices.

BACKGROUND

Certain medical devices, such as catheters and ports, are inserted or implanted into the body. During insertion or implantation, bacteria, for example, from the skin, can be transferred to the insertion site and cause an infection. The infection can spread from the insertion site and become systemic, thereby exposing the body to a health risk.

Methods of treating the infection include administering an antibiotic. The antibiotic can be delivered systemically or locally.

SUMMARY

In one aspect, the invention features a method of treating a medical device. The method includes introducing a liquid antimicrobial agent into the medical device.

In another aspect, the invention features a medical system including a syringe system. The syringe system includes a housing having a first compartment and a second compartment. The first and second compartments are capable of being in fluid communication. The first compartment includes a first composition, and the second compartment includes a second composition. The first and second compositions are capable of reacting to form an antimicrobial agent.

In another aspect, the invention features a medical system, including a syringe system. The syringe system includes a first syringe having a first composition, and a second syringe having a second composition. The first and second compositions are capable of forming an antimicrobial agent.

Embodiments can include one or more of the following. The method can include actuating a syringe system having a first composition and a second composition. The first and second compositions are capable of forming an antimicrobial agent. The first and second compositions can form the antimicrobial agent in the syringe system. The first and second compositions can form the antimicrobial agent in the medical device. The antimicrobial agent can be introduced into a wall or a lumen of the medical device. The antimicrobial agent can include iodine. The medical device can be selected from the group consisting of a catheter, a port, and a wound drain. The catheter can be selected from the group consisting of a urinary catheter, a venous catheter, an arterial catheter, a dialysis catheter, a balloon catheter, a central venous catheter, and a pediatric catheter.

The first and second compartments can be arranged in series or in parallel relative to an outlet of the housing. The syringe system can further include a third compartment capable of being in fluid communication with the first and second compartments. The medical system can further include a medical device having a portion capable of being introduced into a patient. The medical device can be selected from the group consisting of a catheter, a port, and a wound drain. The catheter can be selected from the group consisting of a urinary catheter, a venous catheter, an arterial catheter, a dialysis catheter, a balloon catheter, and a pediatric catheter. The medical device can include a chamber capable of being in fluid communication with the first and second compartments. The first composition can include an oxidant and/or an iodide. The second composition can include an oxido-reductase and/or an iodate. The antimicrobial agent can include a proton source. The antimicrobial agent can include an anti-coagulant. The antimicrobial agent can include a viscosity increasing agent.

The syringe system can further include a compartment capable of being in fluid communication with the first and second syringes. The compartment can be attached to the syringes. The compartment can be attached to a medical device different than the syringe system. The system can further include a medical device having a portion capable of being introduced into a patient. The medical device can be selected from the group consisting of a catheter, a port, and a wound drain. The catheter can be selected from the group consisting of a urinary catheter, a venous catheter, an arterial catheter, a dialysis catheter, a balloon catheter, and a pediatric catheter. The first composition can include an oxidant. The first composition can include an iodide. The second composition can include an oxido-reductase. The second composition can include an iodate. The antimicrobial agent can include a proton source. The antimicrobial agent can include an anti-coagulant. The antimicrobial agent can include a viscosity increasing agent.

Embodiments may include one or more of the following advantages. Treating, e.g., disinfecting, the medical device with one or more antimicrobial agents can reduce or prevent infection, thereby reducing or eliminating the need for post-infection treatment. When the antimicrobial agent(s) is in liquid form, a relatively high concentration of the antimicrobial agent(s) can be delivered to the medical device, for example, relative to a solid antimicrobial agent. Liquid antimicrobial agents can be relatively easy to use with relatively little handling, for example, relative to some solid antimicrobial agents that can be inconvenient and/or impractical to use, particularly with devices having a long lumen. Less handling of the agent(s) can reduce the likelihood of contamination. Furthermore, delivering antimicrobial agents immediately after preparation can reduce (e.g., minimize) loss in concentration of antimicrobial agents, e.g., by minimizing absorption of antimicrobial agents by the devices used for preparation, delivery and storage of the agents. The systems can deliver antimicrobial agents immediately after preparation, and the agents can have enhanced effectiveness.

The details of one or more embodiments of the invention are set forth in the accompanying drawings and the description below. Other aspects, features, and advantages of the invention will be apparent from the description and drawings, and from the claims.

DETAILED DESCRIPTION

Figures 1A, 1B:
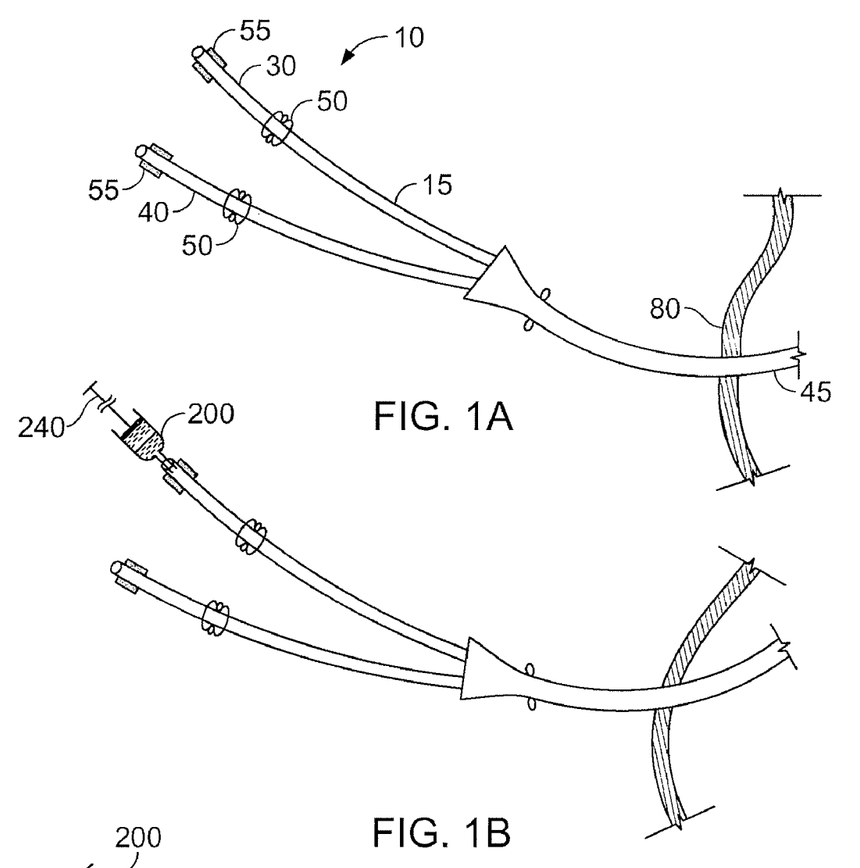
FIGS. 1A, 1B, and 1C illustrate an embodiment of a method of treating a medical device
Figure 1C:
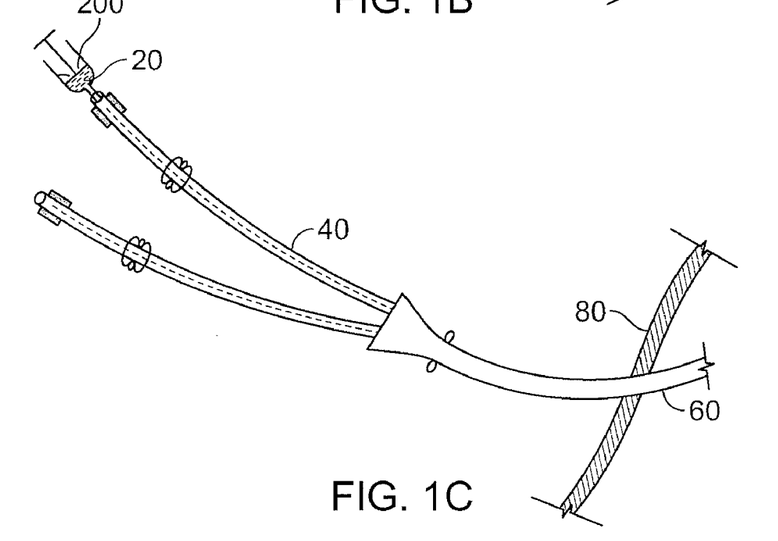

FIGS. 1A-1C illustrate a method 12 of treating, e.g., disinfecting, a medical device 10. As shown, medical device 10 is a dialysis catheter 15 having a portion 45 placed inside a body beneath skin 80. Catheter 15 is treated by delivering a liquid antimicrobial agent 20 from a syringe system 200 into the catheter (FIGS. 1B and 1C). Antimicrobial agent 20 is capable of disinfecting the interior of catheter 15 to reduce the likelihood of microbial activity. In some cases, antimicrobial agent 20 can diffuse to the outer surface of catheter 15 to further reduce microbial activity and/or reduce infection within the body. By using a liquid antimicrobial agent, antimicrobial agent 20 can be conveniently delivered to device 10 with relatively little handling. Reducing handling can further reduce the likelihood of contamination and/or infection.

Referring particularly to FIG. 1A, in some embodiments, catheter 15 is a conventional dialysis catheter having an inlet tube 30 and an outlet tube 40 that communicate with portion 45. Each tube 30 and 40 includes a clamp 50 and a fitting 55, e.g., a Luer fitting or a septum, at the proximal end of the tube. Clamps 50 are used to open or to close their respective tubes. Fittings 55 are used to provide a tight seal between catheter 15 and syringe system 200 (described below). Suitable catheters are, for e.g., dialysis catheters (Vaxcel® chronic dialysis catheter), non-valved central venous catheters (Vaxcel® tunneled central venous catheters), valved central venous catheters (PASV® tunneled central venous catheters) non-valved peripherally inserted central catheters (Vaxcel® PICC peripherally inserted central catheters), valved peripherally inserted central catheters (PASV® PICC peripherally inserted central catheters, and Vaxcel® PICC with PASV® valve technology) or valved ports (PASV® implantable ports) and non-valved ports (Vaxcel® standard mini and micro implantable access systems) available from Boston Scientific Corp. (Natick, Mass.). These medical devices can be made of materials such as polyurethane, ethyl vinyl acetate or silicone. Different grades and blends of polyurethane, e.g. polycarbothane, can also be used. Catheter 15 can be placed in the body according to conventional methods.

Syringe system 200 is generally configured to deliver antimicrobial agent 20 to medical device 10. In some embodiments, syringe system 200 contains two compositions that are isolated from each other. When syringe system 200 is actuated, the two compositions are allowed to combine to form antimicrobial agent 20, which is subsequently delivered to medical device 10. The antimicrobial agent is absorbed by the material of the medical device 10, leaving a solution devoid of antimicrobial agent. This solution can be flushed out of the device. The syringe system 200 can be made of materials that do not absorb antimicrobial agents, e.g., polyethylene terepthalate.

Figure 2A:
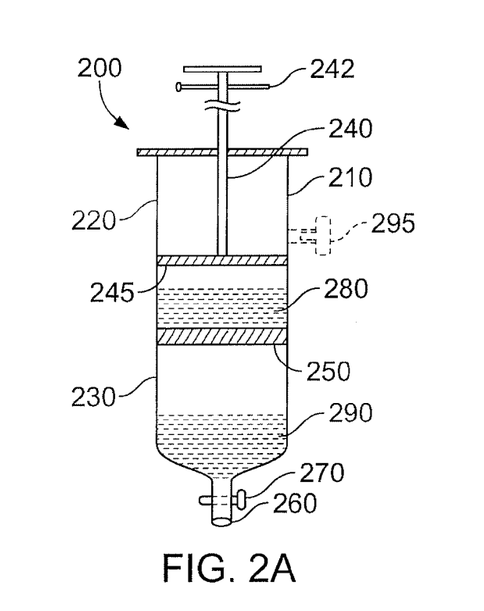
FIG. 2A is a cross-sectional schematic of an embodiment of a syringe system.

Referring now to FIG. 2A, an embodiment of syringe system 200 containing two compositions arranged in series is shown. Syringe system 200 includes a housing 210 defining a proximal compartment 220, a distal compartment 230, and an outlet 260, e.g., a Luer-type fitting, fitted with a stopcock 270. Distal compartment 230 is separated from proximal compartment 220 by a separator 250. Proximal compartment 220 contains a first composition 280, and distal compartment 230 contains a second composition 290.

Compositions 280 and 290 are capable of reacting together to form antimicrobial agent 20. In some embodiments, first composition 280 includes an oxidant. Suitable oxidants include, for example, halide compounds, iodine-containing compounds, and/or thiocyanate compounds. Halide compounds can be, for example, chloride, bromide, and/or iodide compounds. Iodine-containing compounds can be, for example, alkali and/or alkaline earth metal iodides, alkali metal iodates, and/or iodine pentoxide. Alkali metal salts can be, for example, sodium and/or potassium salts. Alkaline earth metal salts can be, for example, calcium and/or barium salts.

Second composition 290 can include an oxidizing agent or a reducing agent. Suitable oxidizing agents include, for example, iodine-oxide salts, peracids and/or substrate oxidoreductases. Suitable iodine-oxide salts include, for example, alkali or alkaline earth metal iodates and/or iodine pentoxide. Suitable peracids can be, for example, perborates and organic peroxyacids. Suitable reducing agents include, for example, ascorbate salts, thiols, and/or organic aldehydes. Thiols can be, for example, cysteine, cysteinylglycine, and homocycteine. The concentration of iodide and iodate salts can be in the range of 0.1-50 mM.

In some embodiments, first and second compositions 280 and 290 react in the presence of protons to produce antimicrobial agent 20, for example, elemental iodine, hypohalites, haloamines, thiocyanogen, and/or hypothiocyanite. The protons can be generated, for example, from hydrolysis of anhydrides, from reaction of enzymes on a substrate, and/or from organic or inorganic acids. Suitable anhydrides include, for example, acetic, maleic, succinic, and/or maleic-succinic anhydride. Suitable enzymes include, for example, glucose oxidase, and tyrosine phosphatase. Suitable organic acids include, for example, citric, succinic, ascorbic, acetic, and iodoacetic acid. Suitable inorganic acids include, for example, hydrochloric, phosphoric, and nitric acid. The amount of acid added can be such that the final pH of the solution is in the range of ~3-6. Water soluble acrylic acid polymers, e.g., carbopol, in the concentration range of 0.05-1% by weight, can also be used as a proton source. Further details of forming antimicrobial agent 20 can be found in U.S. Ser. No. 09/585,911, entitled "Methods and Devices for Providing Anti-infective Activity to a Medical Device", and filed on Jun. 2, 2002, the entire contents of which are incorporated herein by reference.

As described above, first and second compositions 280 and 290 are isolated from each other by separator 250, which is disposed between proximal and distal compartments 220 and 230. Separator 250 provides a liquid-tight seal between compartments 220 and 230. Separator 250 is also configured to preferentially fail at predetermined regions upon application of pressure so that compositions 280 and 290 can combine to form antimicrobial agent 20. As a result, antimicrobial agent 20 can be formed as needed, which can be advantageous because the potency of certain antimicrobial agents, for example, an antimicrobial oxidant, can decrease with time.

Figure 2B:
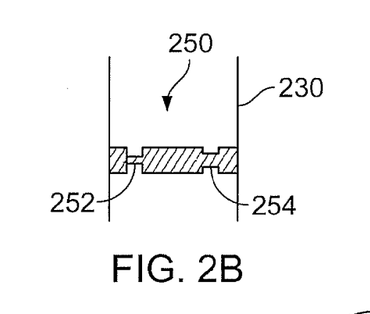
FIG. 2B is a detailed cross-sectional view of an embodiment of a separator of the syringe system of FIG. 2A.
Figure 2C:
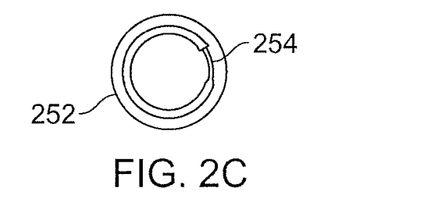
FIG. 2C is a top view of the separator of FIG. 2B.
Figure 2D:
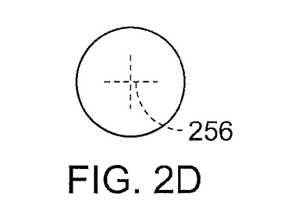
FIG. 2D is a top view of an embodiment of a separator of the syringe system of FIG. 2A.
Figure 2E:
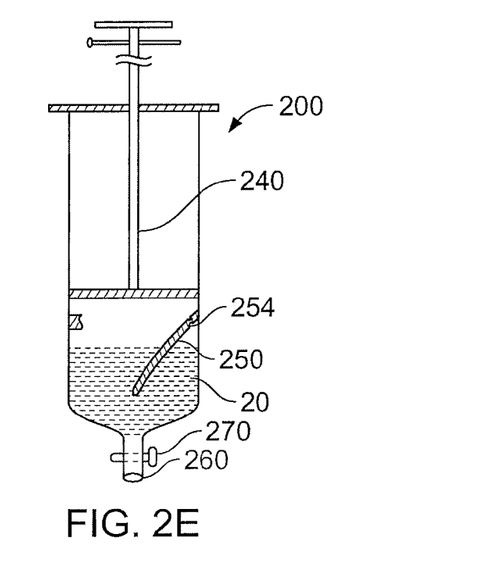
FIG. 2E illustrates actuation of the syringe system of FIG. 2A having the separator of FIG. 2B.
Figure 2F:
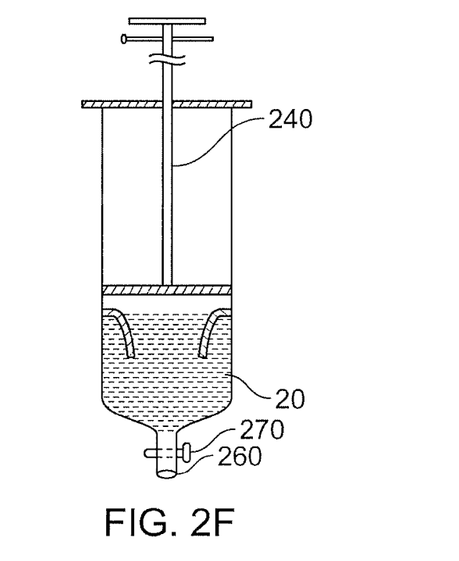
FIG. 2F illustrates actuation of the syringe system of FIG. 2A having the separator of FIG. 2D.

Generally, separator 250 includes one or more regions that are configured to fail, e.g., weaken and rupture, upon application of pressure. In some embodiments, the region(s) can be regions of reduced thickness. For example, referring to FIGS. 2B and 2C, in some embodiments, separator 250 includes a failure region 252 that extends substantially around the perimeter of the separator, and a hinge region 254 that extends along a short segment of the perimeter. As shown, failure and hinge regions 252 and 254 are regions of reduced thickness, e.g., relative to other regions of separator 250. In particular, the thickness of failure region 252 is less than the thickness of hinge region 254 such that separator 250 can preferentially fail at failure region 252 and bend at hinge region 254 (FIG. 2E). FIG. 2D shows another embodiment of separator 250 having a weakened region 256 that can preferentially fail at the center of the separator (FIG. 2F). In certain embodiments, separator 250 can be made of a polymer material or cellulose-based materials, such as cellulose acetate. Failure region 252 or weakened region 256 can be formed by scoring, heating, or laser ablation.

Referring again to FIG. 2A, syringe system 200 further includes a plunger 240 having a plunger lock 242 and a plunger base 245. Plunger lock 242 is used to prevent accidental actuation of plunger 240 and can be placed anywhere along the plunger. Plunger base 245, particularly its perimeter, can be made of a flexible material, such as a rubber or an elastomeric polymer. As a result, plunger base 245 can deflect or bend when it engages separator 250 so that the plunger base can be moved distal of the separator and into distal compartment 230 for delivery of antimicrobial agent 20 into medical device 10.

In operation, catheter 15 is implanted into the body and used according to conventional methods (FIG. 1A). Tubes 30 and 40 are sealed by their corresponding clamps 50. When a disinfecting treatment is desired, e.g., after a dialysis procedure, syringe system 200, with its stopcock 270 closed, is actuated by depressing plunger 240 distally. As plunger 240 is depressed, the plunger applies pressure to separator 250 and ruptures the separator, e.g., at failure region 252 or 256. As a result, first and second compositions 280 and 290 can, combine and form antimicrobial agent 20. For further mixing of compositions 280 and 290, plunger 240 can be drawn proximally, causing antimicrobial agent 20 to back fill proximal compartment 220.

Syringe system 200 is then coupled to tube 30 or 40 of catheter 15 by fitting 55 and outlet 260 (FIG. 1B). Stopcock 270 and the appropriate clamp 50 are then opened. Plunger 240 is depressed further distally, and antimicrobial agent 20 is passed through outlet 260 and into tube 30 or 40 (FIG. 1C). After delivery, syringe system 200 is decoupled from catheter 15 and the appropriate clamp 50 is closed. In some embodiments, the untreated tube of catheter 15 can be treated as described above.

Numerous other embodiments of syringe systems and medical devices can be used.

For example, housing 210 can include a vent valve 295. As shown in phantom lines in FIG. 2A, vent valve 295 can be coupled to proximal compartment 220 to enable pressure control in syringe system 200.

Figure 3A:
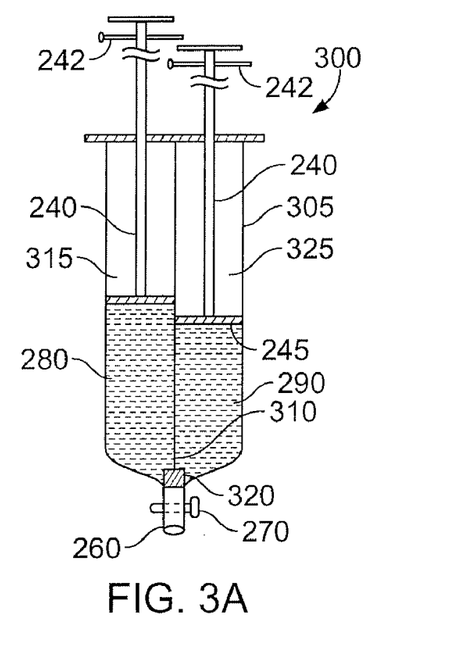
FIG. 3A is a cross-sectional schematic of an embodiment of a syringe system.

FIG. 3A shows an embodiment of a syringe system 300 containing two compositions 280 and 290 arranged in parallel. Syringe system 300 includes a housing 305 defining a first compartment 315, a second compartment 325, and an outlet 260 in fluid communication with both compartments. Outlet 260 includes a stopcock 270. First compartment 315 contains first composition 280, and second compartment 325 contains second composition 290. Compartments 315 and 325 are separated from each other by a separator 310 but are capable of being in fluid communication through a pressure-activated, two-way valve 320 of the separator. Valve 320 can include a breakable polymer membrane that can flex into either compartment 315 or 325, based on the pressure differential between the compartments. Syringe system 300 further includes two plungers 240 (with corresponding locks 242) located in compartments 315 and 325.

Figure 3B:
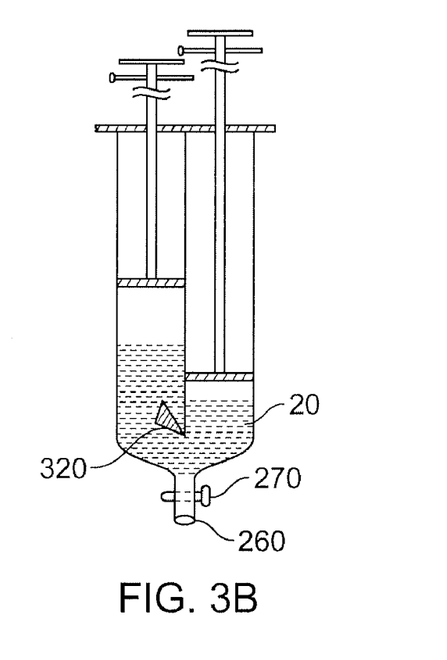
FIG. 3B illustrates actuation of the syringe system of FIG. 3A.

Referring to FIG. 3B, in use, syringe system 300 is actuated by depressing a plunger 240 of second compartment 325 (or first compartment 315) distally. Stopcock 270 is closed. Depressing plunger 240 applies pressure to valve 320, which breaks and flexes into first compartment 325 (or second compartment 325). As a result, first and second compositions 280 and 290 are allowed to mix and to form antimicrobial agent 20. Further mixing can be achieved by repeated, alternating actuation of plungers 240.

System 300 is then coupled to device 10, and stopcock 270 is opened. Plungers 240 are depressed, simultaneously or sequentially, to deliver antimicrobial agent 20 via outlet 260 into medical device 10 as generally described above. In other embodiments, valve 320 can include a failure membrane as described above for separator 250.

Figure 4A:
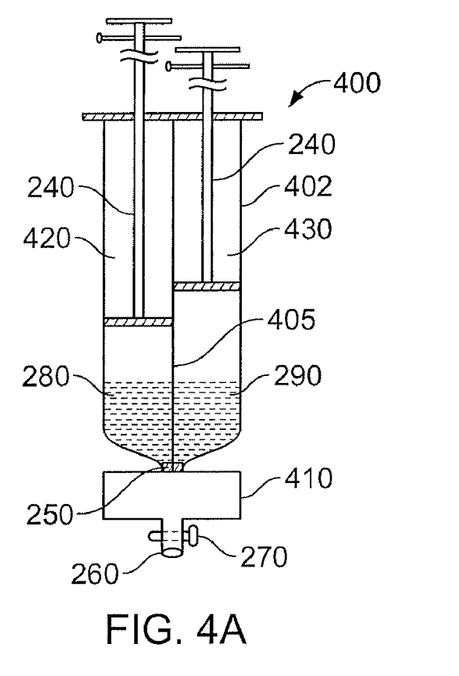
FIG. 4A is a cross-sectional schematic of an embodiment of a syringe system.

FIG. 4A shows an embodiment of a syringe system having two compartments arranged in parallel and capable of being in fluid communication with a mixing chamber. Syringe system 400 includes a housing 402 defining a first compartment 420 and a second compartment 430, and a mixing chamber 410. Compartments 420 and 430 are separated from each other by a divider 405, and are separated from mixing chamber 410 by separator 250. First compartment 420 includes first composition 280, and second compartment 430 includes second composition 290, as described above. System 300 further includes plungers 240, an outlet 260 in fluid communication with mixing chamber 410, and a stopcock 270, generally the same as described above.

Figure 4B:
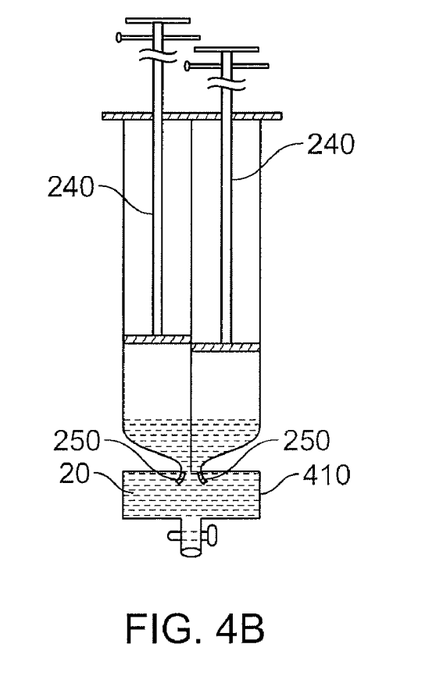
FIG. 4B illustrates actuation of the syringe system of FIG. 4A.

In operation, referring to FIG. 4B, plungers 240 are depressed, simultaneously or sequentially, thereby causing separator 250 to rupture as described above. As a result, first and second compositions 280 and 290 are allowed to flow into mixing chamber 410 and to form antimicrobial agent 20. System 300 is then coupled to medical device 10, and stopcock 270 is opened to allow antimicrobial agent 20 to pass through outlet 260 and into the medical device.

Figure 5A:
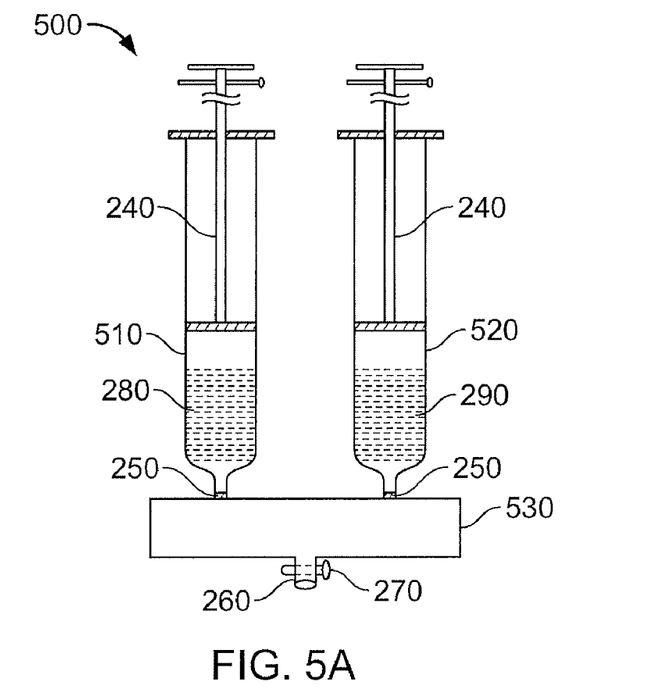
FIG. 5A is a cross-sectional schematic of an embodiment of a syringe system.

FIG. 5A shows a syringe system 500 having two separate syringes 510 and 520 capable of being in fluid communication with a mixing chamber 530. Syringe 510 contains first composition 280, and syringe 520 contains second composition 290. Syringes 510 and 520 are separated from mixing chamber 530 by separators 250. System 500 further includes plungers 240, an outlet 260 in fluid communication with mixing chamber 530, and a stopcock 270, generally the same as described above.

Figure 5B:
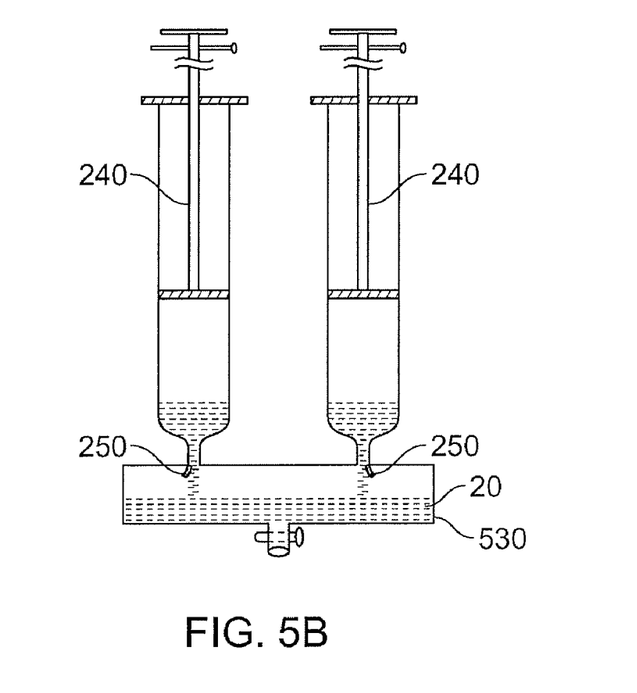
FIG. 5B illustrates actuation of the syringe system of FIG. 5A.

In operation, referring to FIG. 5B, plungers 240 of syringes 510 and 520 are depressed, sequentially or simultaneously, thereby causing separators 250 to rupture. As a result, first and second compositions 280 and 290 are allowed to flow into mixing chamber 530 and to form antimicrobial agent 20. System 500 is then coupled to medical device 10, and stopcock 270 is opened to allow antimicrobial agent 20 to pass through outlet 260 and into the medical device.

Figure 6A:
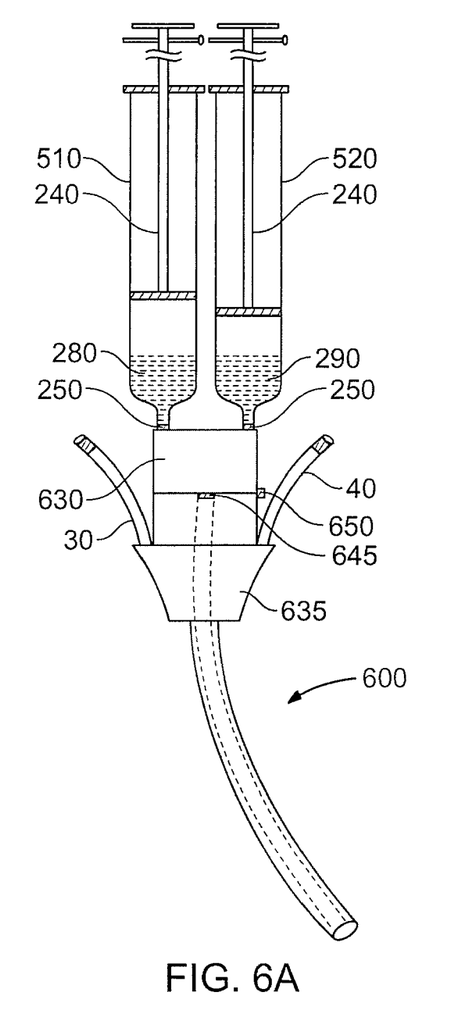
FIG. 6A is a cross-sectional schematic of an embodiment of a syringe system and a medical device.

In some cases, a mixing chamber can be integrally formed on a medical device. Referring to FIG. 6A, a catheter 600, as shown, a dialysis catheter, includes a mixing chamber 630 and a third tube 635 capable of being in fluid communication with the mixing chamber. Third tube 635 is made of a liquid permeable material, for example, poly (dimethyl siloxane) (PDMS), such that antimicrobial agent 20 delivered to the third tube (described below) can diffuse to inlet tube 30 and outlet tube 40 of catheter 600. Third tube 635 is separated from mixing chamber 630 by a slide valve 645, e.g., a spring-loaded valve operable externally through a pusher 650. As shown, mixing chamber 630 is coupled to syringe system 500 through separators 250.

Figure 6B:
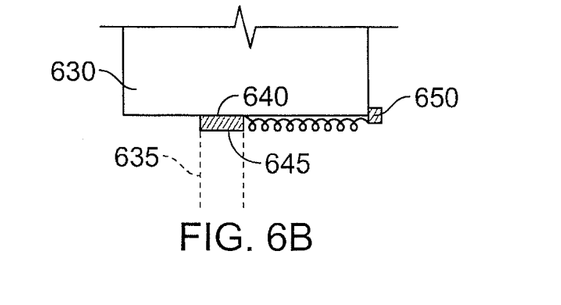
FIGS. 6B-6D illustrate actuation of the syringe system of FIG. 6A.
Figure 6C:
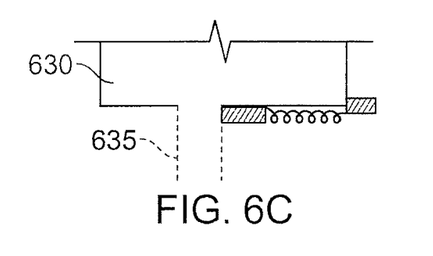
Figure 6D:
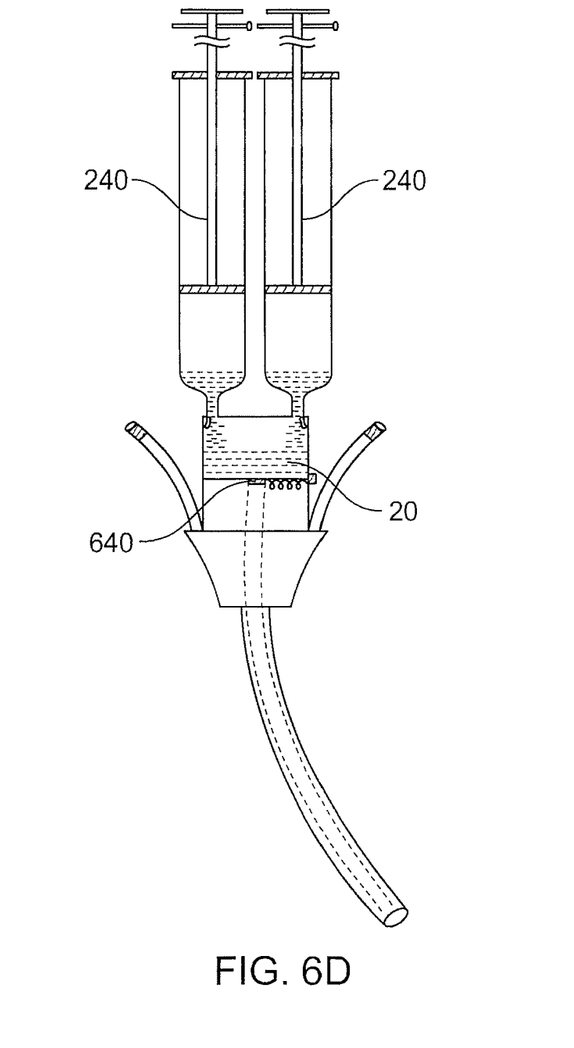

In operation, referring to FIGS. 6B-6D, with slide valve 645 closed, syringe system 500 is actuated by depressing plungers 240. As a result, separators 250 rupture, and first and second compositions 280 and 290 are allowed to flow into mixing chamber 630 and to form antimicrobial agent 20. To deliver antimicrobial agent 20 from mixing chamber 630 into catheter 600, slide valve 645 is opened, and the antimicrobial agent is allowed to flow into third tube 635 of catheter 600. Antimicrobial agent 20 then diffuse through the permeable wall of third tube 635 and into inlet and outlet tubes 30 and 40. In some cases, the wall of third tube 635 can be constructed to be selectably permeable to a predetermined tube, e.g., inlet tube 30 or outlet 40.

Figure 7A:
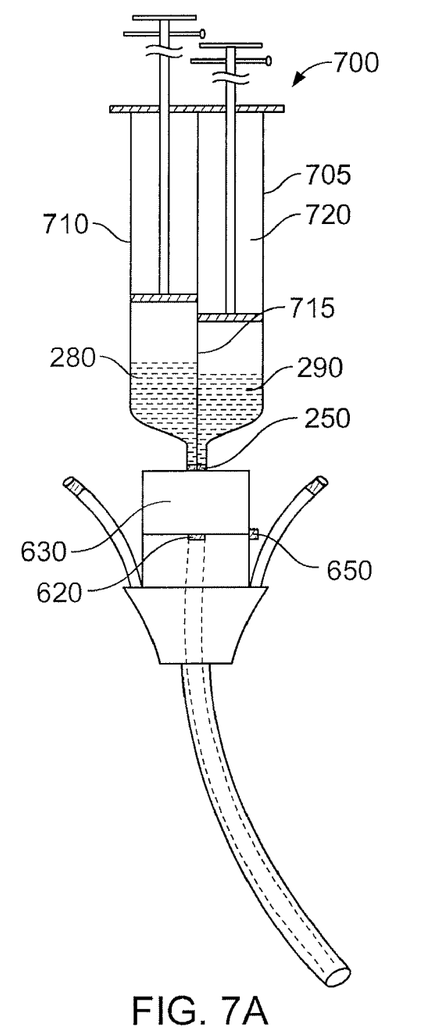
FIG. 7A is a cross-sectional schematic of an embodiment of a syringe system and a medical device.
Figure 7B:
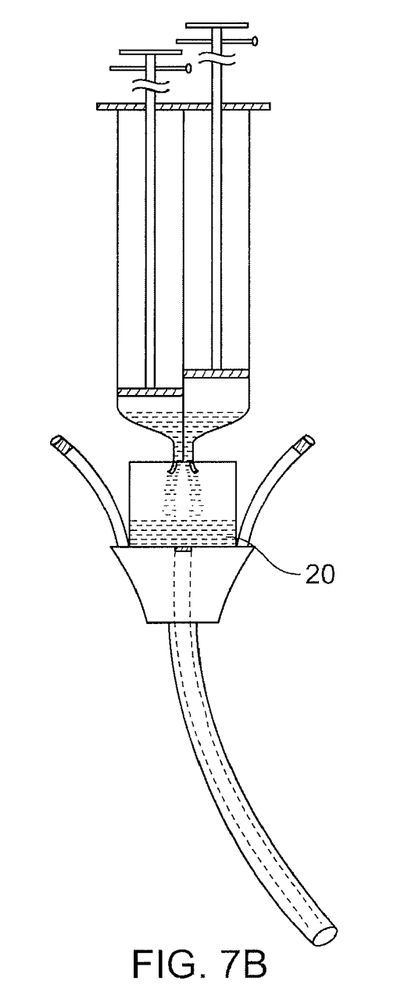
FIG. 7B illustrates actuation of the syringe system of FIG. 7A.

In other embodiments, other syringe systems described herein can be used with catheter 600. For example, FIG. 7A shows a catheter 700 generally the same as catheter 600 coupled to syringe system 400. FIG. 7B shows catheter 700 and syringe system 400 in operation.

Mixing chambers similar to mixing chamber 630 can be included in other medical devices, such as, ports, dialysis catheters, and central venous access catheters.

Still other suitable syringe systems are described, for example, in U.S. Pat. Nos. 5,971,953; 5,817,056; 5,685,846; and 4,613,326, all hereby incorporated by reference in their entirety.

Figure 8:
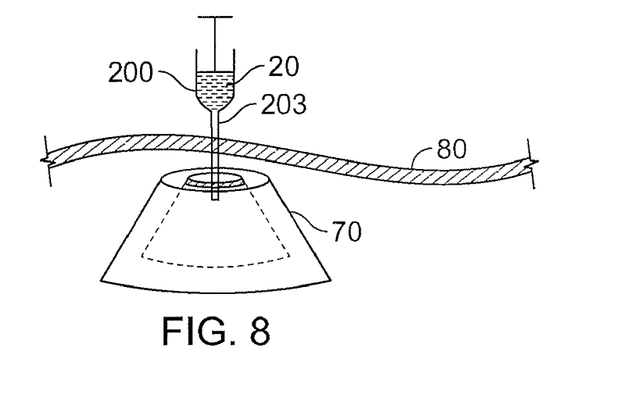
FIG. 8 illustrates an embodiment of a method of treating a medical device.

In other embodiments, method 12 can be applied to other types of medical devices. For example, referring to FIG. 8, syringe system 200 can be used to deliver antimicrobial agent 20 to a port 70 wholly implanted beneath skin 80. As shown, syringe system 200 includes a needle 203 to deliver antimicrobial agent 20 from housing 210 to port 70. Other suitable medical devices include, for example, wound drains, vascular grafts, and other types of catheters. Suitable catheters can be, for example, urinary, venous, arterial, balloon, pediatric, drainage or micro catheters.

Antimicrobial agent 20 can be delivered to medical device 10 prior to and/or after insertion or implantation of the device into the body. In some cases, less handling of medical device 10 is involved when antimicrobial agent 20 is delivered after the device has been inserted or implanted into the body. Antimicrobial agent 20 can be delivered into a wall of medical device 10 for sustained release of the agent over time. Device 10 can include, for example, a wall made of a polymer such as polyurethane, ethylvinyl acetate, or polycarbothane silicone.

In certain embodiments, antimicrobial agent 20 can further include an additive. For example, antimicrobial agent 20 can include an anticoagulant, such as heparin, to prevent clotting. Alternatively or in addition, antimicrobial agent 20 can include a viscosity enhancing substance, such as carbopol, to reduce, e.g., inhibit, expulsion of the antimicrobial agent from medical device 10.

Other embodiments are within the scope of the following claims.

What is claimed is:

1. A medical system, comprising:
    a syringe system comprising:
        a housing having a first compartment and a second compartment, the first and second compartments capable of being in fluid communication; and
        a plunger having a plunger base disposed within the housing, the plunger adapted to apply pressure to fluid in the housing; and
        a membrane disposed between the first compartment and the second compartment, the membrane limiting fluid communication between the first compartment and the second compartment, the membrane breakable to allow contents of the first compartment to mix in the housing with contents of the second compartment;
    wherein the first and second compartments are arranged in series relative to an outlet of the housing; and
    wherein the membrane includes an annular region with reduced thickness relative to a thickness of a central region of the membrane, the annular region comprising a first region of reduced thickness configured to preferentially fail and a second region of reduced thickness which is thicker than the first region of reduced thickness, the first region of reduced thickness extending around a first portion of a perimeter of the membrane and the second region of reduced thickness extending around a second portion of the perimeter of the membrane.

2. The system of claim 1, wherein the syringe system further comprises a third compartment capable of being in fluid communication with the first and second compartments.

3. The system of claim 1, further comprising a medical device having a portion capable of being introduced into a patient.

4. The system of claim 3, wherein the medical device comprises a chamber capable of being in fluid communication with the first and second compartments.

5. The system of claim 1, wherein the medical device is selected from the group consisting of a catheter, a port, and a wound drain.

6. The system of claim 5, wherein the catheter is selected from the group consisting of a urinary catheter, a venous catheter, an arterial catheter, a dialysis catheter, a balloon catheter, and a pediatric catheter.

7. The system of claim 1, wherein the first composition comprises an oxidant.

8. The system of claim 1, wherein the first composition comprises an iodide.

9. The system of claim 1, wherein the second composition comprises an oxido-reductase.

10. The system of claim 1, wherein the second composition comprises an iodate.

11. The system of claim 1, wherein the antimicrobial agent comprises an proton source.

12. The system of claim 1, wherein the antimicrobial agent comprises an anti-coagulant.

13. The system of claim 1, wherein the antimicrobial agent comprises a viscosity increasing agent.

* * * * *

UNITED STATES PATENT AND TRADEMARK OFFICE
CERTIFICATE OF CORRECTION

PATENT NO. : 7,435,237 B2
APPLICATION NO. : 10/453144
DATED : October 14, 2008
INVENTOR(S) : Sharon Mi Lyn Tan It is certified that error appears in the above-identified patent and that said Letters Patent is hereby corrected as shown below:

Column 8, line 56, in claim 11, delete "an" and insert --a--.

Signed and Sealed this

Thirtieth Day of December, 2008

JON W. DUDAS
*Director of the United States Patent and Trademark Office*